United States Patent
Ewaldsson et al.

(10) Patent No.: US 11,606,991 B2
(45) Date of Patent: Mar. 21, 2023

(54) GRIP STRENTHENING SUPPORT DEVICE

(71) Applicant: Bioservo Technologies Aktiebolag, Kista (SE)

(72) Inventors: Martin Oskar Gustaf Ewaldsson, Sigtuna (SE); Johan Ingvast, Åkersberga (SE)

(73) Assignee: BIOSERVO TECHNOLOGIES AKTIEBOLAG, Kista (SE)

( * ) Notice: Subject to any disclaimer, the term of this patent is extended or adjusted under 35 U.S.C. 154(b) by 1155 days.

(21) Appl. No.: 16/304,156

(22) PCT Filed: May 29, 2017

(86) PCT No.: PCT/EP2017/062934
§ 371 (c)(1),
(2) Date: Nov. 22, 2018

(87) PCT Pub. No.: WO2017/207509
PCT Pub. Date: Dec. 7, 2017

(65) Prior Publication Data
US 2020/0315271 A1  Oct. 8, 2020

(30) Foreign Application Priority Data
May 30, 2016  (SE) .................................. 1650752-7

(51) Int. Cl.
*A41D 19/015*  (2006.01)
*A41D 13/08*  (2006.01)
(Continued)

(52) U.S. Cl.
CPC ..... *A41D 19/01547* (2013.01); *A41D 13/087* (2013.01); *A41D 19/01582* (2013.01);
(Continued)

(58) Field of Classification Search
CPC ........ A41D 19/01547; A41D 19/01582; A41D 13/087; A61F 5/0118; A61F 5/013;
(Continued)

(56) References Cited

U.S. PATENT DOCUMENTS 8,029,414 B2 * 10/2011 Ingvast .................. B25J 9/0006
601/40
2008/0000010 A1  1/2008 Erickson
(Continued)

FOREIGN PATENT DOCUMENTS

WO  2008027002 A1  3/2008

OTHER PUBLICATIONS

International Search Report and Written Opinion from corresponding International Application No. PCT/EP2017/062934, dated Jul. 26, 2017; 10 pages.
(Continued)

*Primary Examiner* — Keri J Nelson
(74) *Attorney, Agent, or Firm* — Tucker Ellis LLP

(57) ABSTRACT

A grip strengthening device having a finger portion for enhancing the grip by means of at least one artificial tendon arranged along at least one finger portion, wherein the finger portion comprises material along both sides and a tip, and possible along a dorsal side, the at least one artificial tendon is attached along both sides so that the artificial tendon may move, wherein the artificial tendon runs closer to a ventral side than the dorsal side of the finger portion, at least at positions corresponding to joints of a wearer's finger, the finger portion will transfer a force to provide a movement of the finger when the artificial tendon is retracted, wherein the artificial tendon runs in a detour towards or to a position in the middle between the dorsal and ventral side or closer to the dorsal side at a proximal portion of the finger portion.

10 Claims, 3 Drawing Sheets

(51) Int. Cl.
*A61F 5/01* (2006.01)
*A61H 1/02* (2006.01)

(52) U.S. Cl.
CPC .......... *A61F 5/0118* (2013.01); *A61H 1/0288* (2013.01); *A61F 2005/0155* (2013.01)

(58) Field of Classification Search
CPC ......... A61F 5/05875; A61F 2005/0155; A61H 1/0288; A63B 23/16
See application file for complete search history.

(56) References Cited

U.S. PATENT DOCUMENTS

| | | |
|---|---|---|
| 2010/0249675 A1 | 9/2010 | Fujimoto |
| 2012/0029399 A1 | 2/2012 | Sankai |
| 2015/0328492 A1* | 11/2015 | Marriott ................. A63B 23/14 482/124 |

OTHER PUBLICATIONS

International Preliminary Report on Patentability from corresponding International Application No. PCT/EP2017/062934, completed May 15, 2018; 19 pages.

* cited by examiner

GRIP STRENTHENING SUPPORT DEVICE

TECHNICAL AREA

The present invention concerns a grip strengthening support device having at least one finger portion for enhancing the grip for at least one corresponding finger of a wearer by means of at least one artificial tendon arranged along at least one finger portion of the grip strengthening support device.

BACKGROUND ART

There are previously known grip strengthening support devices, for example shown in WO 2008/027002. In this document a finger glove for grip strengthening is shown, having at least one glove finger with at least one artificial tendon on the inside of the glove finger on both sides of the glove finger and the artificial tendon runs in a duct attached on the inside of the glove finger. When a pulling force is applied to the artificial tendon the glove finger will bend towards the palm of the glove, i.e. the ventral side of the glove.

One problem is the way the at least one artificial tendon moves during pulling of the artificial tendon in relation to the glove and a hand of the wearer. During the pulling of the at least one artificial tendon the glove finger and a finger positioned inside of it will bend towards a ventral side of the glove and into a gripping position. At the transition between the glove finger and glove palm the artificial tendon tend to move inwards the centre of the bent glove finger leaving a space between the artificial tendon and a hand of a wearer. Thus the glove will also be moved inwards the centre. Thus the glove may be in the way when gripping, for example. Additionally, it is uncomfortable for the wearer.

SUMMARY OF THE INVENTION

The aim of the present invention is to diminish the above problems. According to an aspect of the present invention a grip strengthening support device having at least one finger portion for enhancing the grip for at least one corresponding finger of a wearer by means of at least one artificial tendon arranged along at least one finger portion of the grip strengthening support device. The finger portion comprises material at least along both sides and a tip, and possible along a dorsal side, corresponding to a finger of a wearer. The at least one artificial tendon is attached along both sides of a finger portion so that the artificial tendon may move in its length direction in respect to the sides of the finger portion. The artificial tendon runs along the side closer to a ventral side than the dorsal side of the finger portion, at least at positions corresponding to joints of a wearer's finger, so that the finger portion will transfer a force in order to provide a movement of the wearer's finger towards a gripping position when the at least one artificial tendon is retracted. The artificial tendon runs in a detour towards or to a position in the middle between the dorsal and ventral side or closer to the dorsal side at a proximal portion of the finger portion. Because of this detour the artificial tendon will run closer to the palm of the wearer during gripping.

According to an embodiment the at least one artificial tendon is attached by means of loops or at least partly by means of tunnels fixedly arranged at the material, at least in the vicinity of the positions corresponding to joints of a wearer's finger and the detour. Thus the path of the artificial tendon may be controlled in an effective way in order to provide the desired function and result. It is also conceivable that the at least one artificial tendon runs in a full tunnel along the full side of the finger portion.

According to an embodiment the at least one artificial tendon is attached at the tip of the finger portion slightly towards the ventral and dorsal side and are running along a thought straight line coming closer to the ventral side when coming closer to the proximal portion of the finger portion, where the detour is positioned, when the finger portion is straight.

According to an embodiment the finger portion is made up with a material having the at least one artificial tendon arranged on the outside thereof. Preferably, the finger portion is made up with a stretchable material having at least one patch of non-stretchable material arranged on the outside of the stretchable material, where the at least one artificial tendon is arranged at the at least one patch. Both of these embodiments may have the at least one finger portion covered by means of a glove like device.

According to an embodiment the material of the finger portion is provided by a finger of a glove like device, where the at least one artificial tendon is arranged at the inside of the glove like device.

According to an embodiment one artificial tendon is provided at a first side of the finger portion over the tip and along a second side of the finger portion and is retractable or pullable in both ends in order to cause a gripping position.

According to an alternative embodiment a first artificial tendon is provided along a first side of the finger portion and fixed to a tip portion and a second artificial tendon is provided along a second side of the finger portion and fixed to the tip portion, wherein both the first and second artificial tendons are retractable or pullable in their ends in order to cause a gripping position. Preferably in any of the embodiments the end of the at least one artificial tendon is retractable or pullable by means of an actuator.

SHORT DESCRIPTION OF THE DRAWINGS

The present invention will now be described in more detailed under referral to attached drawings, in which:

FIG. 1 shows a view of an embodiment of a finger portion and an artificial tendon running along the side of the finger portion.

FIG. 2a-b show a schematic view of different paths for an artificial tendon.

DETAILED DESCRIPTION OF EMBODIMENTS

Figure 1:
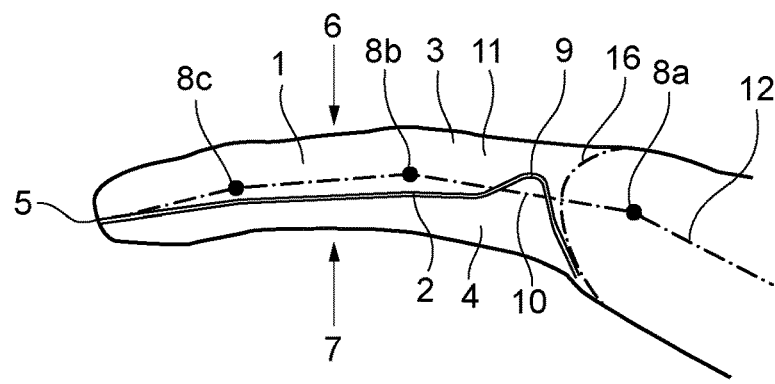

In FIG. 1 it is shown a view of an embodiment of a grip strengthening support device having at least one finger portion 1 for enhancing the grip for at least one corresponding finger of a wearer by means of at least one artificial tendon 2 arranged along at least one finger portion 1 of the grip strengthening support device. The shown finger portion may for example be suitable for a middle finger of a wearer's hand. The finger portion 1 comprises material 3 at least along both sides 4 and a tip 5, and possible along a dorsal side 6, corresponding to a finger of a wearer, the at least one artificial tendon 2 is attached along both sides 4 of a finger portion 1 so that the artificial tendon 2 may move in its length direction in respect to the sides 4 of the finger portion 1. The finger portion 1 may be suitable for any of the fingers of a wearer's hand including the thumb.

Figure 6:
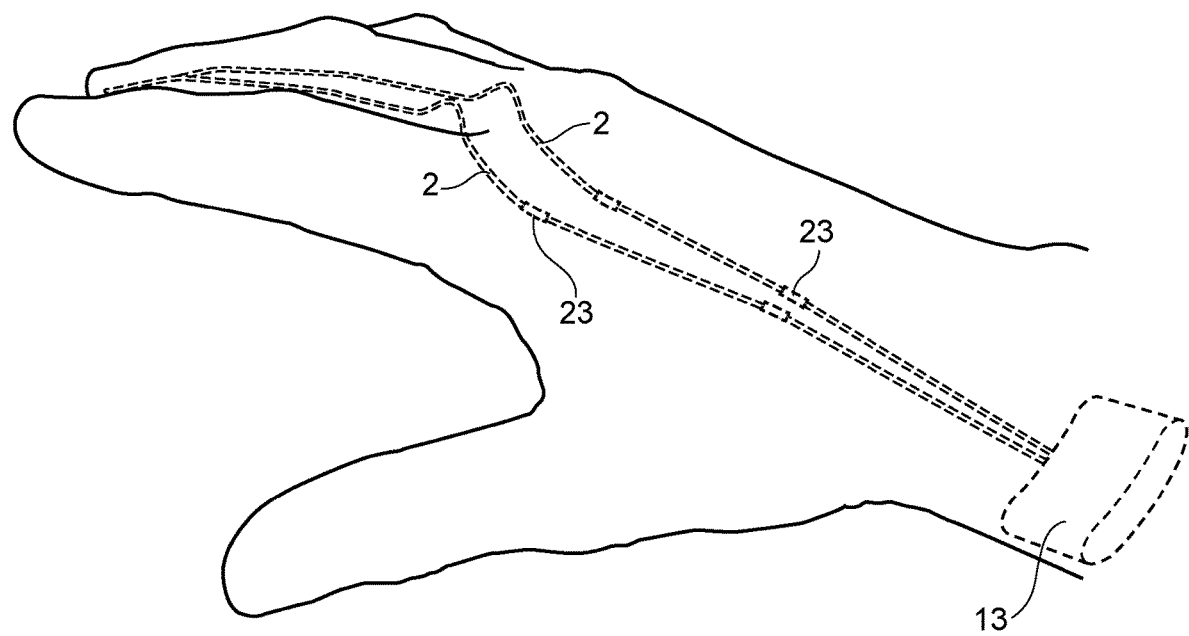
FIG. 6 shows an embodiment of a grip strengthening support device having an actuator for pulling artificial tendons.

The artificial tendon 2 runs along the side 4 closer to a ventral side 7 than the dorsal side 6 of the finger portion 1, at least in the vicinity of positions 8a-c corresponding to joints of a wearer's finger, so that the finger portion 1 will transfer a force to the wearer's finger in order to provide a movement of the wearer's finger towards a gripping position, i.e. the finger moves inwards the palm of the wearer's hand, when the at least one artificial tendon 2 is retracted or pulled by means of an actuator 13. This is shown in FIG. 6.

The artificial tendon 2 runs in a detour 9 towards or to a position 10 in the middle between the dorsal 6 and ventral 7 side or closer to the dorsal 6 side at a proximal portion 11 of the finger portion 1. The detour 9 is positioned between two positions 8a and 8b corresponding to the joints of a wearer's finger, where the first position 8a corresponds to the joint at the proximal end of the finger at the palm and the second position 8b corresponds to the joint at the other end of that piece of phalangeal bone of the wearer's hand. The position 10 is situated at a thought line 12 dividing the finger portion side 3 in two portions, the dorsal 6 and the ventral 7 portion.

Figure 2A:
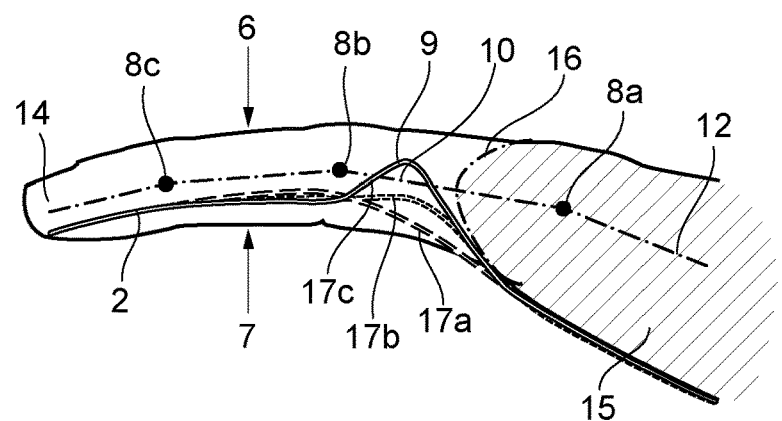

In FIG. 2a a schematic view of different routes for an artificial tendon 2 is shown when a finger of a wearer is straight and in line with a palm of the wearer. For clarity reasons the grip strengthening support device, such as a glove like device, is not shown. The thought line 12 goes from the first position 8a corresponding to the joint at the proximal end of the finger 14 at the palm 15 and the second position 8b corresponding to the joint at the other end of that piece of phalangeal bone of the wearer's hand. The thought line 12 continues further out to the distal position 8c corresponding to the distal joint of the wearer's finger. The thought line runs along the phalanges of the wearer's finger. The piece of material 16 of a finger glove corresponding to the piece of skin present between fingers of a hand is shown in the figure.

Three paths 17a-c for the artificial tendon 2 is shown schematically. Path 17a shows the path of the artificial tendon 2 of known grip strengthening devices. Path 17b shows a path where the detour 9 runs towards a position 10 in the middle between the dorsal 6 and ventral 7 side, towards the thought line 12. Path 17c shows a path where the detour 9 runs closer to the dorsal 6 side, i.e. crosses the thought line 12.

Figure 2B:
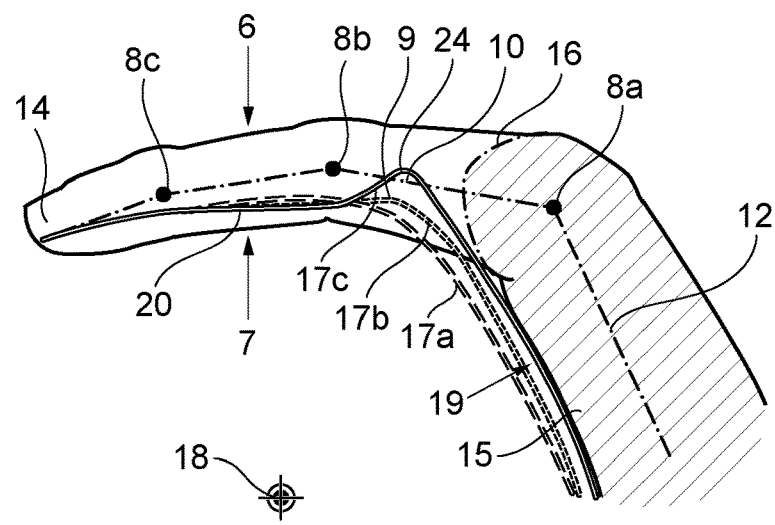

FIG. 2b shows the finger 14 of a wearer is bent towards the palm 15 of the wearer, the ventral side 7. For clarity reasons the grip strengthening support device, such as a glove like device, is not shown. In this figure it is schematically shown how the different paths 17a-c differ during bending. The previously known path 17a strives inwards a thought centre 18 of a gripping position. Along the finger portion 1 a counteracting force is applied by means of at least a portion of a dorsal side 6 of the finger portion 1 holding the artificial tendon 2 in place. At the piece of skin 16 between fingers of a hand it is not possible to provide this counteracting force leading to the shown space 19 between the palm 15 of the wearer and the artificial tendon 2. At the outer sides 4 of the index finger and the little finger, respectively it is not necessary having a detour as counteracting forces may be applied from the dorsal side 7.

According to the invention a detour 9 is provided. Two variants of detours are shown as paths 17b-c in FIG. 2b, which are providing a closer position of the artificial tendon 2 to the palm 15 of the wearer. Path 17b showing a path where the detour 9 runs towards a position 10 in the middle between the dorsal 6 and ventral 7 side, towards the thought line 12, gives a closer position of the artificial tendon 2 to the palm 15 of the wearer than the previously known path 17a.

Path 17c showing a path where the detour 9 runs closer to the dorsal 6 side, i.e. crossing the thought line 12, give an even closer position of the artificial tendon to the palm 15 of the wearer than path 17b. On the other hand path 17c might give rise to another effect of the artificial tendon 2. It will strive towards the dorsal side 6 between 8b and 8c. In this case it is important to provide a counteractive support on the ventral side 7 of the finger portion 1.

It is thus possible to provide the artificial tendon 2 in a detour 9 in any conceivable path 17 towards or to a position 10 in the middle between the dorsal 6 and ventral 7 side or closer to the dorsal 6 side at a proximal portion 11 of the finger portion 1. A top 24 of the detour 9 may be positioned as close to the proximal end of the finger portion 1 as possible, i.e. as close to the skin piece 16 of a wearer's hand when in use, in order to have the closest travel of the at least one artificial tendon 2 towards the palm of a wearer during gripping.

According to an embodiment shown in FIG. 1 the at least one artificial tendon 2 is attached at a tip 5 of the finger portion 1 close to the middle between the ventral 7 and dorsal 6 side and are running along a thought straight line coming closer to the ventral 7 side on its path to the detour 9 is positioned. FIG. 1 shows when the finger portion 1 is straight.

Figure 3:
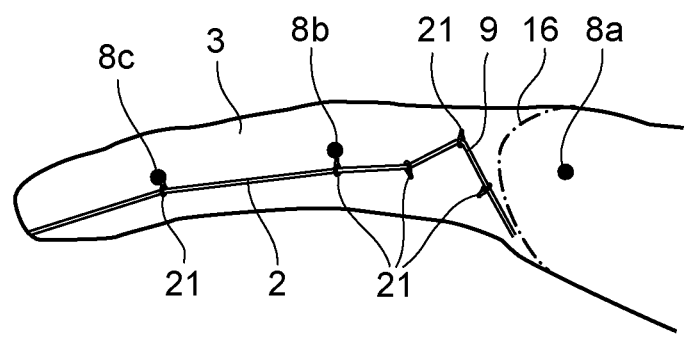
FIG. 3 shows a view of loops arranged at an embodiment of a finger portion through which an artificial tendon may run.
Figure 4:
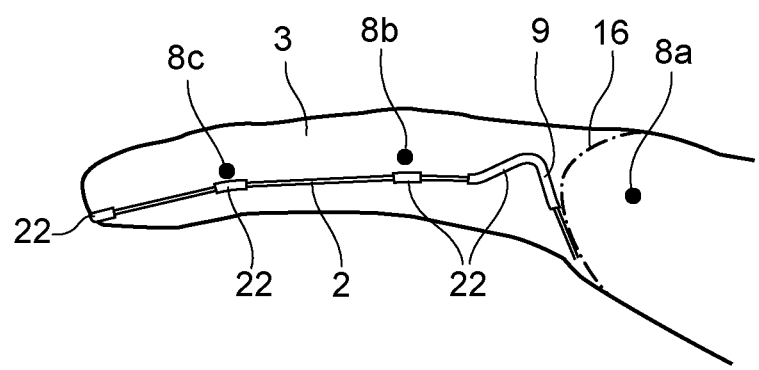
FIG. 4 shows a view of tunnels arranged at an embodiment of a finger portion through which an artificial tendon may run.

In order to provide the desired path 17 for the artificial tendon 2 it may be controlled by means of loops 21 through which the artificial tendon 2 travels. This is shown in the exemplified embodiment in FIG. 3. Preferably, loops 21 are arranged at the material 3 at least in the vicinity of the positions 8 corresponding to the joints of a wearer's finger and at the detour 9. In FIG. 4 it is instead shown tunnels 22 for the artificial tendon 2 to travel through. These tunnels 22 may be short and preferably positioned at the material 3 at least in the vicinity of the positions 8 corresponding to the joints of a wearer's finger, or between the positions 8, and at the detour 9. But it is also conceivable having tunnels 22 running along the full side 3 of the finger portion 1 including the detour 9. The shown finger portion in FIGS. 3 and 4 may for example be suitable for a middle finger of a wearer's hand.

An artificial tendon 2 may run from an actuator 13 via one or several guides 23 (see FIG. 6) towards a finger portion 1 and distally along a first side 4 of the finger portion 1 to the distal end of the finger portion 1, the tip 5, and back proximally along the second side 4 of the finger portion 1 via one or several guides 23 to the actuator 13. It also possible to have two artificial tendons 2 for one finger portion 1 where a first artificial tendon 2 runs from the actuator 13 via one or several guides 23 towards a finger portion 1 and distally along a first side 4 of the finger portion 1 to the distal end of the finger portion 1, the tip 5, where it is attached, preferably at the first side 4, to a tip portion 5 of the finger portion 1. On the opposite side, the second side 4, a second artificial tendon 2 is attached and it runs along the second side 4 of the finger portion via one or several guides 23 to the actuator 13.

Figure 5:
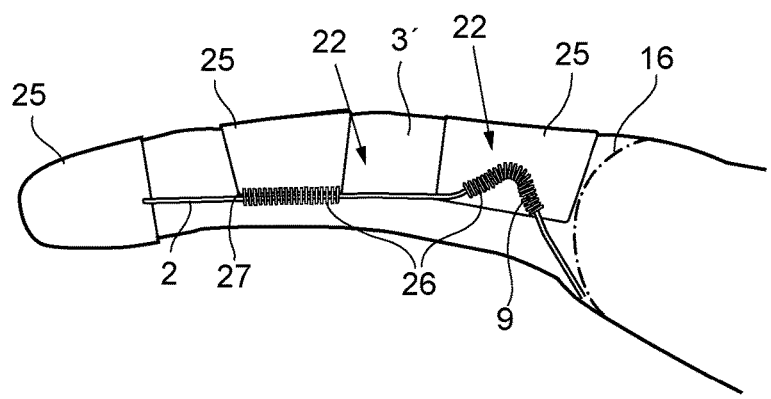
FIG. 5 shows an embodiment of a finger portion having patches thereon where the artificial tendon is arranged at the patches.

According to one embodiment the finger portion 1 is made up with a material having the at least one artificial tendon 2 arranged on the outside thereof. According to a special embodiment of this, the finger portion 1 is made up with a stretchable material 3' having at least one patch 25 of non-stretchable material arranged on the outside of the stretchable material 3'. An example of this is shown in FIG. 5.

The at least one artificial tendon 2 is arranged at the at least one patch 25. In the shown example a tunnel 22 for the artificial tendon 2 is made up by stitches 26 along an edge 27 of the patches 25. Thus the artificial tendon 2 can run in these tunnels 22 in a controlled way making up a desired path 17. When the artificial tendon or tendons 2 are pulled by means of the actuator 13 the patches 25 will transfer the bending forces to a finger present in the finger portion 1. The patches 25 will also form a counteractive support during a gripping movement so that the artificial tendons 2 will not leave its path. Preferably, the at least one finger portion is covered by means of a glove like device. The glove like device is provided with one or several guiding means 23 for the artificial tendons 2 and an actuator 13 for pulling of the artificial tendons 2.

According to another embodiment the material 3 of the finger portion 1 is provided by a finger of a glove like device, where the at least one artificial tendon 2 is arranged at the inside of the glove like device.

The invention claimed is:

1. A grip strengthening support device for enhancing the grip of a finger of a wearer, the grip strengthening support device comprising:
   a finger portion having a tip, opposing lateral sides, a dorsal side, and a ventral side; and
   an artificial tendon arranged along the finger portion of the grip strengthening support device,
   wherein the finger portion comprises material along both lateral sides of the finger portion and the tip of the finger portion, and the finger portion having a joint position on each lateral side configured to be positioned laterally adjacent each pivot point of each knuckle of the wearer's finger and a joint of the wearer's finger with a palm of the wearer, a curved plane projected through each joint position dividing the dorsal side of the finger portion and the ventral side of the finger portion,
   wherein the artificial tendon is moveably attached to the material along both lateral sides of the finger portion so that the artificial tendon moves longitudinally relative to the finger portion,
   wherein the artificial tendon extends longitudinally along each lateral side along a path that, at the joint positions, is on the ventral side of the finger portion so that retraction of the artificial tendon causes the finger portion to move the wearer's finger towards a gripping position of the wearer's finger,
   wherein the path of the artificial tendon further comprises a detour between the joint positions corresponding to the proximal joint of the wearer and the joint positions corresponding to the joint of the wearer's finger with the wearer's palm, the detour altering the path of the artificial tendon to be one of:
   closer the dorsal side of the finger portion at the detour than at the joint positions corresponding to the proximal joint of the wearer, or
   on the dorsal side of the finger portion at the detour, and
   wherein the path of the artificial tendon is further configured to extend along the palm of the wearer.

2. The grip strengthening support device according to claim 1, wherein the artificial tendon is attached to the material with at least one loop or by at least one tunnel, the at least one loop or the at least one tunnel fixedly arranged to the material adjacent a corresponding one of the joint positions or the detour.

3. The grip strengthening support device according to claim 1, wherein the artificial tendon is further attached at the tip of the finger portion, the path of the artificial tendon being closer to the division between the dorsal and proximal sides at the tip than at a distal end of the detour.

4. The grip strengthening support device according to claim 1, wherein the artificial tendon is arranged on an outside of the material.

5. The grip strengthening support device according to claim 4, wherein the finger portion is covered by a glove like device.

6. The grip strengthening support device according to claim 1, wherein the material of the finger portion comprises a stretchable material and a patch of non-stretchable material arranged on an outside of the stretchable material, wherein the artificial tendon is attached to the patch.

7. The grip strengthening support device according to claim 1, wherein the finger portion is provided by a finger of a glove like device, where the artificial tendon is arranged at an inside of the glove like device.

8. The grip strengthening support device according to claim 1, wherein the path of the artificial tendon extends along the lateral sides and the tip, and the artificial tendon is retractable at both ends thereof.

9. The grip strengthening support device according to claim 8, further comprising an actuator that retracts the ends.

10. The grip strengthening support device according to claim 1, wherein the artificial tendon comprises a first tendon portion that extends along a first of the lateral sides of the finger portion and is fixed to the tip and a second tendon portion that extends along a second of the lateral sides of the finger portion and is fixed to the tip, wherein both the first and second portions are retractable at respective ends.

* * * * *